(12) United States Patent
Schreckenberg et al.

(10) Patent No.: US 9,069,063 B2
(45) Date of Patent: Jun. 30, 2015

(54) METHOD FOR RECORDING MEDICAL IMAGES OF A MOVING OBJECT

(75) Inventors: Marcus Schreckenberg, Freising (DE); Christian Galuschky, Munich (DE); Georg Schummers, Munich (DE); Horst Joachim Mayer, Munich (DE); Alexander Rossmanith, Germering (DE)

(73) Assignee: TOMTEC IMAGING SYSTEMS GMBH (DE)

( * ) Notice: Subject to any disclaimer, the term of this patent is extended or adjusted under 35 U.S.C. 154(b) by 799 days.

(21) Appl. No.: 12/993,193

(22) PCT Filed: May 27, 2009

(86) PCT No.: PCT/EP2009/056435
§ 371 (c)(1),
(2), (4) Date: Feb. 22, 2011

(87) PCT Pub. No.: WO2009/144243
PCT Pub. Date: Dec. 3, 2009

(65) Prior Publication Data
US 2011/0262109 A1  Oct. 27, 2011

(30) Foreign Application Priority Data

May 29, 2008   (DE) .......................... 10 2008 025 674

(51) Int. Cl.
*H04N 5/77*   (2006.01)
*G01S 7/52*   (2006.01)
(Continued)

(52) U.S. Cl.
CPC ........... *G01S 7/52046* (2013.01); *A61B 5/0456* (2013.01); *A61B 8/08* (2013.01); *A61B 8/0883* (2013.01); *G01S 7/52088* (2013.01); *G01S 15/8993* (2013.01)

(58) Field of Classification Search
CPC ........... H04N 5/76; H04N 7/163; H04N 7/50; G11B 20/10; G11B 20/10527; G11B 20/1217; G11B 20/18; G11B 20/1883; G11B 7/005; G06K 9/3258
See application file for complete search history.

(56) References Cited

U.S. PATENT DOCUMENTS

| 5,159,931 A | 11/1992 | Pini |
| 5,993,390 A | 11/1999 | Savord et al. |

(Continued)

FOREIGN PATENT DOCUMENTS

| DE | 19732125 | 2/1999 |
| DE | 102005014445 | 10/2006 |

(Continued)

OTHER PUBLICATIONS

International Search Report; PCT/EP2009/056435; Aug. 19, 2009.

*Primary Examiner* — Tat Chio
(74) *Attorney, Agent, or Firm* — Cantor Colburn LLP

(57) ABSTRACT

The invention relates to a method for recording medical images, in particular ultrasound images, of a moving object, in particular of a heart, said method comprising the following steps: generating a movement signal that dynamically represents the state of movement of the moving object, identifying the phase position and the frequency of the moving object on the basis of the movement signal, reconstructing the images on the basis of the phase position and of the frequency and/or carrying out at least one scan of the moving object, with the recording times being adjusted according to the phase position and the frequency of the moving object.

9 Claims, 3 Drawing Sheets

(51) Int. Cl.
*A61B 8/08* (2006.01)
*A61B 5/0456* (2006.01)
*G01S 15/89* (2006.01)

(56) References Cited

U.S. PATENT DOCUMENTS

| | | | |
|---|---|---|---|
| 6,673,017 B1 * | 1/2004 | Jackson | 600/437 |
| 6,966,878 B2 * | 11/2005 | Schoisswohl et al. | 600/443 |
| 2005/0238216 A1 * | 10/2005 | Yoden | 382/128 |
| 2008/0240355 A1 * | 10/2008 | Ohishi | 378/98 |

FOREIGN PATENT DOCUMENTS

| | | |
|---|---|---|
| EP | 0736284 | 10/1996 |
| EP | 0813074 | 12/1997 |
| WO | 2006136988 | 12/2006 |

* cited by examiner

METHOD FOR RECORDING MEDICAL IMAGES OF A MOVING OBJECT

TECHNICAL FIELD

The invention relates to a method and a device for recording medical images, in particular ultrasound images of a moving object, in particular a heart.

The invention relates in particular to the problem of performing an image acquisition or recording at a potentially irregularly moving object such as a heart, at a good spatial resolution over several cycles. Furthermore, it is desirable to reduce the recording time.

BACKGROUND

In cardiology, imaging techniques are common which need to record over several cardiac cycles in order to obtain sufficient spatial and temporal resolution. For this reason, images and heartbeat are recorded synchronously, while the images are recorded with a fixed repetition rate.

Especially in echocardiography, currently such methods are common, which select those images that were taken within one cardiac interval from a sequence of consecutive 2D images or 3D volumes. In the following, without loss of generality it is assumed that a cardiac cycle extends accurately from one R-spike of the ECG signal to the next.

The patent DE 197 32 125 relates to a method for recording ultrasound images of moving objects, wherein during the largest movements of the object no or only a few pictures, and at times of less movement of the object several pictures are taken. By coupling the recording times with the ECG of the creature, the systole is omitted, which means that during a short period no pictures are taken, and afterwards multiple images are recorded during the diastole according to the electrocardiogram. This is also possible by continuously recording the organ, during which the data processing system selects suitable images and processes the desired images. Such medical imaging methods or ultrasonic imaging procedures based on electrocardiographic information are also known from U.S. Pat. No. 6,673,017 and U.S. patent application U.S. 2005/0238216. ECG-triggered imaging is described in U.S. Pat. No. 5,159,931. A disadvantage of these methods is that they usually lag behind the movement cycle, i.e. the dead time between the processing of the cardiac cycle and the implementation for the control of the recording times is relatively large.

U.S. Pat. No. 6,966,878 describes a method for recording and processing a volume scan of a periodically moving object. For that purpose a volume scan at a periodically moving object is performed, wherein within the volume scan, a time interval of the periodic motion of the object is identified and afterwards the volume scan is regrouped based on this time interval.

Since the movements of the moving object, such as the repetition of the heartbeat, and the recording times of the images are often asynchronous, and since the movements themselves are not regular, the time of the first recording in each cycle, based on the particular state of motion of the moving object, can be variable. Depending on the acquisition/recording method (nearest or subsequent recording) the range of variation is $[-\Delta t/2 \ldots \Delta t/2]$ or $[0 \ldots \Delta t]$, where $\Delta t$ is the time interval between consecutive recordings. Especially when imaging rapidly and/or irregularly moving objects, this temporal variation leads to artefacts in the subsequent spatial reconstruction.

Therefore pictures of objects that produce a motion blur due to their own movements are usually taken in synchrony to that movement. Without the synchronization to the corresponding movement of the object (stroboscopic imaging), a blurred image, or an image of the object in each of its states of motion, is the result. When recording images in synchrony to the motion of the object (an exact synchronization is currently not possible with the resources of the state of the art), one image is created for each state of motion of the moving object. One example is the three-dimensional ultrasound imaging of the heart. The corresponding images of the heart show successively all stages (phases) between contraction (systole) and relaxation (diastole) of the heart. The successive appearance of individual photographs of the heart corresponds to a four-dimensional representation of the heart, with the fourth dimension representing the corresponding movement of the heart (timeline).

The solution known from DE 197 32 125 therefore relies on combining the recording times of the moving object with the ECG of the creature. That is done e.g. by scanning the patient with ECG electrodes. From the measured ECG a R-spike—or another distinguished point—is determined. The temporal position of the R-spike is used to synchronize continuously taken ultrasound images of the heart to the cardiac cycle, or the acquisition of ultrasound data is started with the detection of the R-spike. The end of the cardiac cycle is then obtained either by using a moving average of the cardiac cycle duration (gained from the R-spikes over time) or the subsequent R-spike is used as the end of the current cardiac cycle. If no ECG is available, the image data must be cut/trimmed manually to a cardiac cycle by the doctor under visual control. Thus, the cycle length can be determined retrospectively from the image content manually or automatically (with appropriate image recognition system).

The ECG electrodes may also peel away, in particular during the stress levels (stress test), so that the ECG cannot be detected and thus the recording of the data is hindered. Furthermore, using electrodes might be costly, since the electrodes themselves are not cheap and their attachment to the patient takes time and creates costs for staff and reduces the throughput of examinations. In case that problems occur with the ECG recording, the manual trimming of the image data causes considerable amount of work by a highly specialized worker.

The solution known from U.S. Pat. No. 6,966,878 B2 is based on the determination of a time interval from the image data, for instance on the basis of certain intensity values or the intensity curve, of a time-based acquisition of ultrasound images during an examination. The time interval is the grid, in which the continuous image data stream is divided into cardiac cycles, i.e. the image data is assigned to a position in the cardiac cycle. The position of the grid, i.e. the phase, is left aside here.

However, a better spatial resolution is desirable in particular with regard to different stress levels. Thus artefacts occurring when recording images in cardiology are prevented/reduced. This is advantageous especially if the object does not behave strictly periodically but only quasi-periodically or even non-periodically, as is often the case when cardiac defects occur. Furthermore, the disadvantages caused by the use of electrodes for ECG are avoided by the synchronization without ECG.

DE 10 2005 014 445 A1 discloses a medical imaging system comprising a control device, at least one image acquisition device and a trigger device. The trigger device, alike the device described in DE 197 32 125, detects the phase angles of the object, for instance the heart, and sequentially sends multiple trigger impulses to the control unit. The trigger pulses all correspond with a predetermined phase position (reference phase) of the object, for instance the start of the systole of the heart. For the typical case where the object is a beating heart, an ECG-triggering is used.

The trigger device of DE 10 2005 014 445 A1 detects only the phase of the object. The starting times for image recording are either identical to the times when activating trigger signals occur or have a predetermined delay time to these times. The detection of the sequences of images is terminated when reaching a stop time point. This means that in certain circumstances, the sequences do not have the same number of images. Although the numbers are about the same, they are not exactly the same. They normally vary by one or two pictures. The control device must therefore modify those sequences which contain a smaller number of images. Furthermore, those images recorded with the same temporal distance to the starting time do not match to the same phase, because they are recorded or evaluated with a constant temporal distance between each other, and thus changing speed of the moving object is not taken into account and artefacts occur.

BRIEF SUMMARY

The invention optimizes the spatial resolution of medical images, in particular ultrasound images of a moving object, and/or to reduce the scan time.

By means of the method according to the invention and the corresponding device, it is possible to place the recording times in synchrony with the phase position and/or the frequency of the moving objects, or rather a respective allocation of the image data is possible, so that each recording time of separate image-sub-regions, which correspond to one state of movement of the object, corresponds to the same state of movement of the heart and can be allocated accordingly. Image planes of the same phase position then correspond with a specific state of movement within the periodic movement of the object. Thus, it is possible, also under the normal variances in the cycle length of successive heartbeats (and partially also in patients suffering from arrhythmia), to obtain accurate images of the separate states of movement of the heart.

Essentially, the method comprises the following steps:
Generating a movement signal that dynamically represents the state of movement of the moving object,
Identifying the phase position and/or the frequency of the moving object on the basis of the movement signal,
Reconstructing the images on the basis of the phase position and/or the frequency and/or carrying out at least one scan of the moving object, with the recording times being adjusted according to the phase position and/or the frequency of the moving objects.

According to a preferred embodiment of the method according to the invention, the movement signal is obtained by means of a first scan of the object: While the device, e.g. the ultrasound probe, is slid along the object in order to record separate image-subregions of the moving object and thereby make recordings of the object at certain points of time, wherein such recordings represent the separate "slices" of the object and are assembled in a data processing system to a three-dimensional volume image, from the image content, the momentary frequency f(t) of the movement and/or the phase position p(t) in time is derived. Preferably, both frequency and phase position are derived. So-called 3D-wobblers can acquire the images automatically, a manual sliding is thereby not necessary anymore.

Of course, the current frequency f(t) of the movement and/or the current phase position p(t) can also be derived from the ECG signal.

The volume image can be obtained by a multitude of techniques (e.g. three-dimensional scanning, 3D-imaging in real time, volume scanning, 2D-scanning with transducers having position sensors, free-hand scanning by means of a volume-element correlation method, 2D- or matrix-array transducers and suchlike).

The position of each volume element is defined by its geometrical accuracy (i.e. the distance from one volume element to the next), by e.g. an ultrasound response and by values derived from the ultrasound response. Suitable ultrasound responses can be e.g. B-, flow-, greyscale, colour-flow values and angio- or power-Doppler data.

In the derivation from the image content, the R-triggers are e.g. replaced by "time points of the same phase position". In one embodiment, the local extrema (maximum or minimum) of the signals are derived, since these can be more easily correlated with the physiological state of the heart (end diastole or end systole). However, the back coupling from the state of movement of the recorded object to the parameter of the recording itself, i.e. frequency and phase position of the image acquisition/recording device, is important.

In mechanical wobblers (and equivalently in electronically controlled matrix probes) a further component is added: Frequency and phase position of the change in position in the direction of elevation (perpendicular to the 2D-image plane).

The recordings/images can now be shifted in synchrony with the frequency and/or phase. Alternatively, the recording times can, in a further scan, be selected in synchrony with the phase position and/or the frequency, so that it is possible to obtain recordings which correspond to the state of movement of the object at the corresponding time point. Image planes of the same phase position then correspond to a particular state of movement, e.g. the end diastole or end systole of the heart, within the periodic movement of the object.

Instead of selecting consecutive recordings from one series, the present invention suggests to synchronize the recording times themselves from the heartbeat. To do this, there are e.g. the following two possibilities:
(1) The image generation is synchronized to the heartbeat, i.e. it is sufficient to shift only the starting time point in synchrony with the R-spike, the recording frequency itself can then be held constant;
(2) In special applications of intra-cardiac echocardiography, the heartbeat can be synchronized to the image generation, e.g. by synchronization of a pacemaker with the image source.

It can be advantageous to adapt also the recording rate to a periodic heart movement. The optimum solution therefore depends on the movement pattern to be recorded. Thereby, firstly, the movement cycle can start with the R-spike, wherein the course in time will remain the same, independently of the respective R-R interval (i.e. the recording rate is constant, but the starting time is variable). Furthermore, the R-R interval can be predetermined (e.g. pacemaker). Secondly, the movement can depend linearly from the R-R interval (i.e. the same number of recordings is done per cycle).

The invention also relates to a suitable device having the following essential means:
Measuring means for generating a movement signal, which dynamically represents the state of movement of the moving object, such as e.g. an ECG device or software means for evaluating a first scan.

Evaluating means for identifying a phase position and/or the frequency of the moving object from the movement signal, and Reconstructing means for reconstructing the images on the basis of the phase position and/or the frequency and/or recording means for carrying out at least one (further) scan of the moving object under adjustment of the recording times in accordance with the phase position and/or the frequency of the moving object.

BRIEF DESCRIPTION OF THE DRAWINGS

Special embodiments will be described with reference to the drawings.

DETAILED DESCRIPTION

Figure 1:
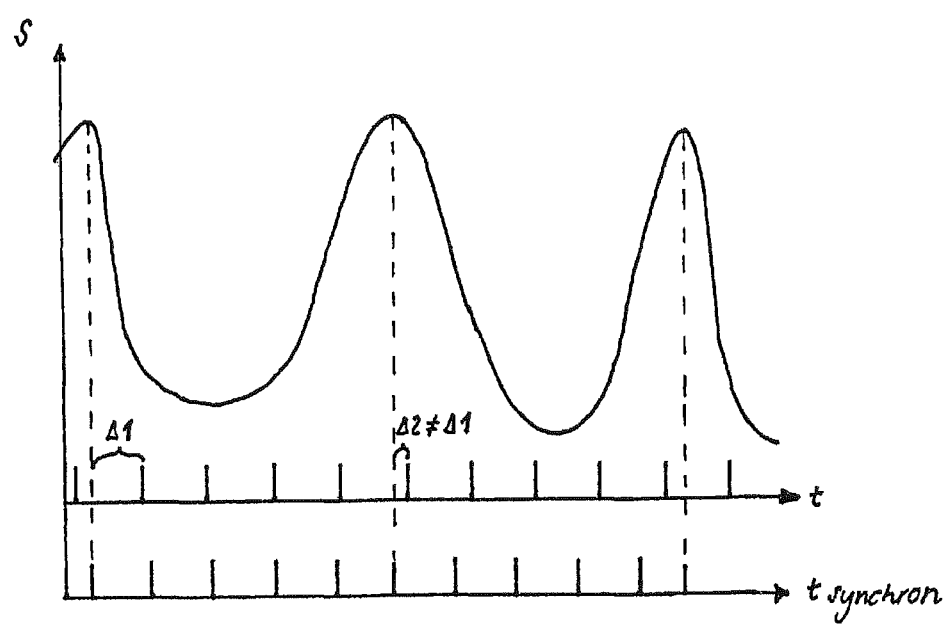
FIG. 1 shows a schematic view of the signal S(t), which has been derived from the image content and the analysis of which furnishes the frequency f(t) and the phase position p(t), the "real" recording times (t) with a variation range Δ(t) and the recording time points ($t_{synchron}$) according to the invention of individual states of movement and their allocation.

FIG. 1 shows a schematic depiction of the signal (S) which has been extracted from the image content of ultrasound recordings of the heart, and the analysis which furnishes the current frequency of the periodic movement f(t) and the phase position in time p(t). Furthermore, the "real" recording times (t) are shown, which are not synchronized and therefore have a variation range Δ(t) (Δ1; Δ2). By back coupling of the state of movement of the heart to the parameters of the recording itself (here the frequency and the phase position of the recording), the recording times can either be back-correlated or in a further ultrasound scan can be synchronized with the frequency and the phase position of the heart ($t_{synchron}$) and thus the spatial resolution of the recording can be increased by a multiple.

Figure 2:
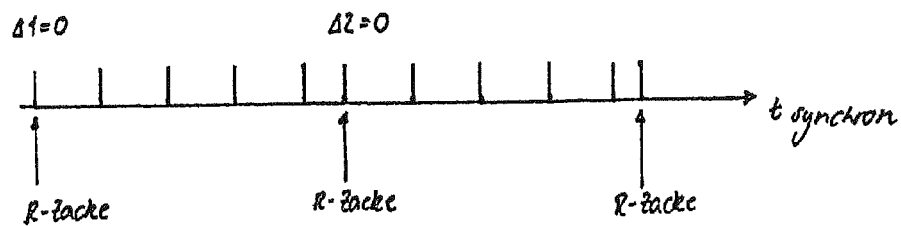
FIG. 2 shows the recording times ($t_{synchron}$) according to the invention, wherein the recording rate is constant and the starting time of the recording is variable.

FIG. 2 shows a variant of the recording times ($t_{synchron}$) in a further ultrasound scan. The recording times ($t_{synchron}$) start with the R-spike of the movement cycle of the heart, wherein, however, the course in time of the recordings remains the same, independent from the R-R interval. Thereby, the recording rate is constant, the starting time is variable. Optionally, the R-R interval or the starting time point can be given/predetermined (e.g. by a pacemaker), so that control of the recording times is achieved by the pacemaker (dynamic image recording).

Figure 3:
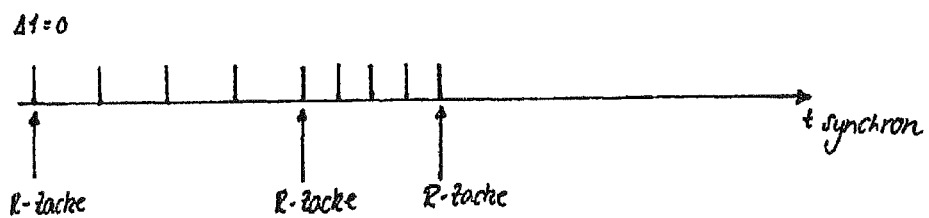
FIG. 3 shows the recording times ($t_{synchron}$) according to the invention, wherein the same number of recordings is carried out within one cycle (=R-R interval).

FIG. 3 shows a further variant of the recording times ($t_{synchron}$) in a further ultrasound scan. The recording time points ($t_{synchron}$) (here 3 equidistant recording times) depend lineally from the R-R interval of the heart, wherein the movement is exactly periodical. Thereby, the same number of recordings per heart cycle results.

Embodiment 1

Figure 4:
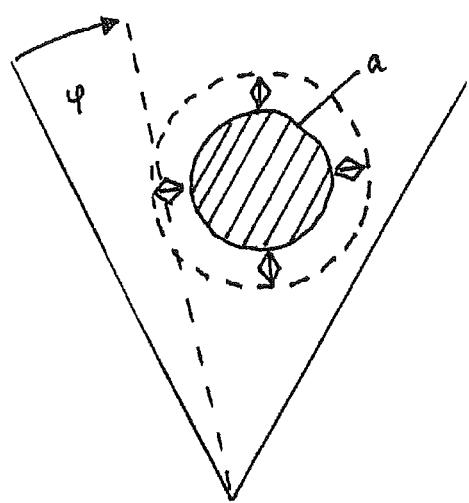
FIG. 4 shows a scan plane with a frequency $f_{scan}$ and the angle position φ in a uni-directional scan, wherein a is the object which pulsates with frequency $f_{object}$.

In the embodiment according to FIG. 4 of the present invention, the frequency of the ultrasound scan ($f_{scan}$) is an integer divisor of the frequency of the moving object ($f_{object}$) (e.g., $f_{object}$=1 Hz, $f_{scan}$=1/10 $f_{object}$) and the relative phase position is constant. The recording is done rotating in a corresponding angle position (=feed). Consequently, the scan plane will intersect the moving object in a certain angle position φ always in the same phase position (=state of movement). Image planes with the same phase position (here 10 images) can then be interpreted as a 3D representation of the state of movement (=time phase of the movement) and be reconstructed accordingly. If subsequently, continuous scans are carried out with a marginally modified phase position, then the same phase position of the object movement is now obtained in other angle positions. If the modification of the phase per scan is suitably selected, consecutive scans can thereby be combined to a volume with a higher angle resolution. If one then increases the frequency $f_{scan}$ to e.g. $f_{scan}$=2× $f_{object}$, one can obtain the original data set with only 20 scans in the same recording time. However, if the image frequency is very high (e.g. 200 Hz), then the method of the present invention, in which the angle feed in relation to the heart movement is 20 times faster than described above, can furnish a data set with 20 planes. Thereby, neighbouring image planes can now be considered as belonging to practically the same state of movement. Thereby, the angle resolution can be increased at identical scan time. However, the method in the state of the art would, at the same image frequency, furnish 2,000 individual images with 200 volumes per heartbeat, but only 10 planes per data set.

Embodiment 1A

In the following example, the heart frequency $f_{object}$=1 Hz and the image frequency $f_{scan}$=2 Hz. The scan angle is 40°, wherein the phase change Δφ is selected such that per scan the corresponding movement phase of the object is reached 2° later. In 10 "heartbeats", one can now accommodate 20 scans, so that 20 planes per 3D-dataset are obtained. As a result, the angle resolution has doubled, wherein the time resolution has been halved to 100 volumina.

Embodiment 1B

At 200 Hz image frequency, 100 images are recorded per scan and separated into 40 blocks. The corresponding time step between two blocks of 12.5 ms is thereby so short that it can be considered as "momentary" for the heart movement. The angle traveled between neighbouring blocks is 1° each. Neighbouring blocks are combined pair-wise and are always defined as being recorded at the same recording point—but with a spatial angle difference of 1°. Thus, per scan 20 time phases with 40 angle positions (1° increment) are generated. If one combines all 20 scans, one obtains 40 different angle positions per 3D-data block at 20 time phases. The angle resolution was again doubled—at the expense of the time resolution.

Embodiment 2

Here, $f_{scan}$ not an integer divisor of $f_{object}$. After recording the ultrasound images, the time phase position p(t) and the current frequency f(t) is derived from the image content. In a further scan, the recording rate remains the same, independent of the respective R-R interval, but the starting time of the recording in relation to the R-spike is varied (see FIG. 2).

Embodiment 3

In an ECG taken under stress of the subject (stress-echo), the heart frequency varies with the different stress levels (e.g.

pulse 60, pulse 120, pulse 140). After recording the ultrasound images, the phase position in time p(t) and the momentary frequency f(t) are derived from the image content. In a further scan, the recording times then depend linearly from the R-R interval, i.e. the same number of recordings is recorded per heart cycle (see FIG. 3). By the present invention, it is possible to record all stress levels "in the same phase", so that all images of the same position can be represented next to each other. Thereby, a significantly improved comparability of the heart images at different stress levels results, since e.g. at a fast heartbeat the same number of images are recorded as at slow heartbeat, i.e. they are recorded faster (in synchrony with frequency), so that for all stress levels, comparable total images are obtained.

The invention claimed is:

1. Method of recording medical images of a heart, the method comprising the steps of:
evaluating an available ECG signal to generate a movement signal that dynamically represents the state of movement of the heart,
identifying the phase position and the frequency of the heart on the basis of the movement signal,
recording images of the heart and reconstructing these images on the basis of the phase position and the frequency of the heart; and
carrying out at least one further scan of the heart wherein rate of recording images is adjusted for each cardiac cycle of the heart such that same number of images are recorded in each cardiac cycle of the heart, wherein each cardiac cycle extends from one R-spike of the ECG signal to the next R-spike of the ECG signal, wherein the heart is moving in irregular cardiac cycles.

2. The method according to claim 1, wherein the recording times are synchronized during the reconstruction of the images based on the frequency and the phase position.

3. The method according to claim 1, wherein during the adjustment of the recording times based on the phase position and the frequency, the recording positions at the heart are adjusted.

4. The method according to claim 1, wherein each further scan are continuous.

5. The method according to claim 1, wherein each further scan is a volume scan.

6. The method according to claim 1, wherein each further scan are carried out by means of 2D or 3D ultrasound devices.

7. The method according to claim 1, wherein image planes of the same phase position correspond to one particular state of movement within the periodical movement of the heart.

8. Device for evaluating medical images of a heart, comprising:
measuring means for evaluating an available ECG signal to generate a movement signal that dynamically represents the state of movement of the heart,
evaluating means for identifying a phase position and the frequency of the heart from the movement signal,
recording means for recording images of the heart and reconstructing these images on the basis of the phase position and the frequency of the heart; and
means for carrying out at least one further scan of the heart wherein rate of recording images is adjusted for each cardiac cycle of the heart such that same number of images are recorded in each cardiac cycle of the heart, wherein each cardiac cycle extends from one R-spike of the ECG signal to the next R-spike of the ECG signal, and wherein the heart is moving in irregular cardiac cycles.

9. Computer-program product comprising program code recorded on a non-transitory computer-readable medium, the program code effecting the performance of the method according to claim 1, when the program code is executed on a computer.

* * * * *